United States Patent [19]

Deindoerfer et al.

[11] 4,393,466
[45] Jul. 12, 1983

[54] METHOD OF ANALYZING PARTICLES IN A DILUTE FLUID SAMPLE

[75] Inventors: Fred H. Deindoerfer, Northridge; Sherman E. DeForest, Encinitas; Gunner Bolz, Del Mar, all of Calif.

[73] Assignee: International Remote Imaging Systems, Chatsworth, Calif.

[21] Appl. No.: 186,418

[22] Filed: Sep. 12, 1980

[51] Int. Cl.³ .............................................. G06F 15/42
[52] U.S. Cl. .................................. 364/415; 356/335; 364/497; 364/555
[58] Field of Search .............. 364/415, 497, 499, 510, 364/515, 555; 356/23, 39, 40, 244, 335; 358/101, 106, 108

[56] References Cited

U.S. PATENT DOCUMENTS

| | | | |
|---|---|---|---|
| 3,591,290 | 7/1971 | Zinner et al. | 356/335 |
| 3,598,907 | 8/1971 | Drinkuth et al. | 358/106 |
| 3,746,784 | 7/1973 | Van Oosterhaut | 358/106 |
| 3,777,169 | 12/1973 | Walter et al. | 358/106 |
| 3,830,969 | 8/1974 | Hofstein | 356/335 |
| 3,941,479 | 3/1976 | Whitehead | 356/335 |
| 4,002,823 | 1/1977 | Van Oosterhout | 358/106 |
| 4,201,470 | 5/1980 | Ehrly et al. | 356/39 |
| 4,205,384 | 5/1980 | Merz et al. | 364/555 |
| 4,220,499 | 9/1980 | Hughes, Jr. et al. | 364/555 |

FOREIGN PATENT DOCUMENTS 1011673 12/1965 United Kingdom .

OTHER PUBLICATIONS

Balston et al., "A CCD Digital Image Store"; Alard Conf. Proc. No. 230, Impact of CCD & Surface Acoustic Wave Devices on Signal Proc. & Imagery . . . "Oct. 1977.
Leach et al., "Description, Performance and Calibration of a CCD Camera", Public. of Astronomical Society of the Pacific; Apr. 1980.

Primary Examiner—Errol A. Krass
Attorney, Agent, or Firm—Limbach, Limbach & Sutton

[57] ABSTRACT

A method for analyzing particles and particularly sediments of urine is accomplished by distributing the sample over an extended area. A plurality of optical still images is taken of the sample, with each image representing a different portion of the area. Each optical image is converted into an electronic image. The plurality of electronic images are composited to form one resultant electronic image.

11 Claims, 4 Drawing Figures

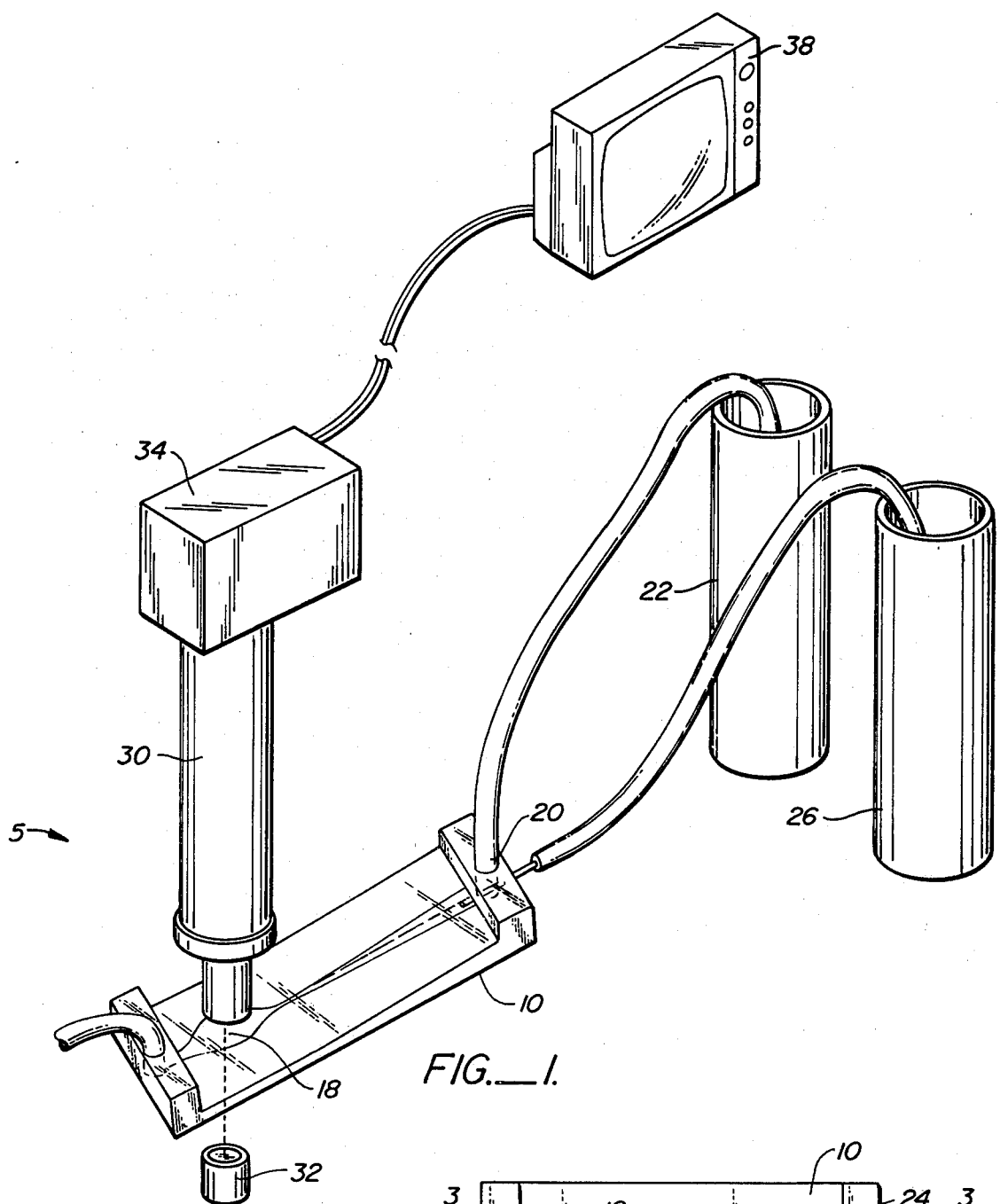
FIG._1.
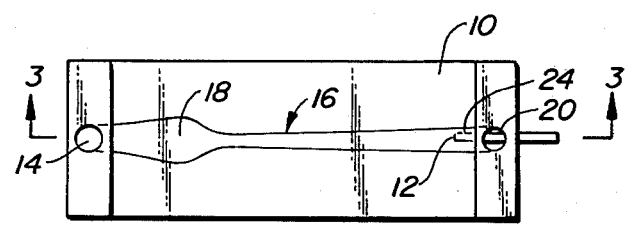
FIG._2.
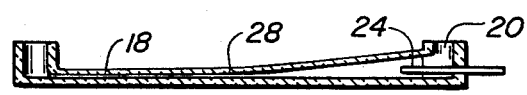
FIG._3.

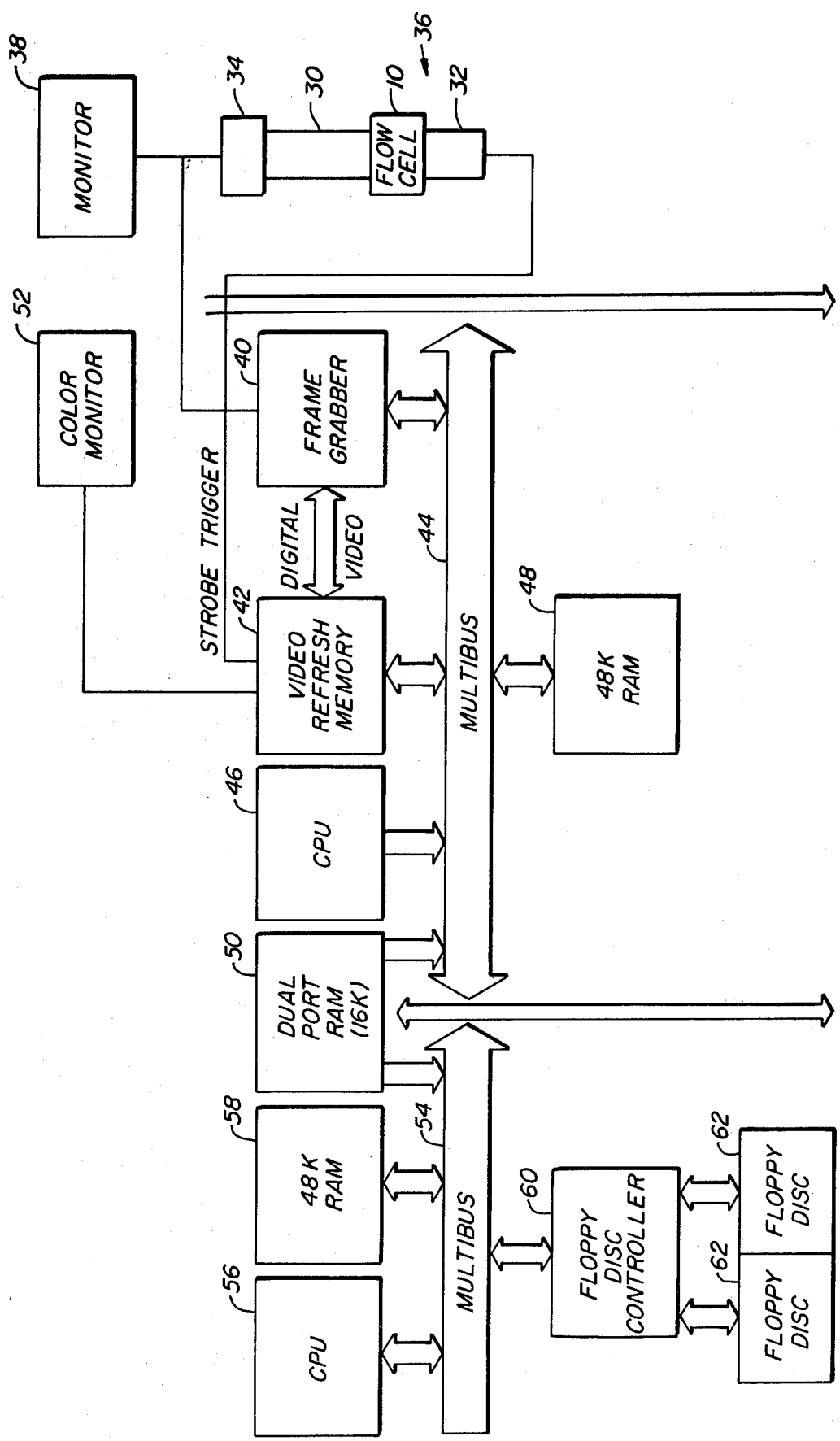
FIG._4.

METHOD OF ANALYZING PARTICLES IN A DILUTE FLUID SAMPLE

BACKGROUND OF INVENTION

The present invention relates to a method of analyzing particles in a fluid sample and more particularly to a method of analyzing biological fluid samples, such as urine, that are dilute, but without the necessity of physically creating a concentrated sample for analysis.

Heretofore the method for urine sediment examination requires the following steps: (i) urine must be poured into a tube and spun down in a centrifuge to separate the sediment from its suspending fluid; (ii) most of the cleared suspending fluid must be poured out; (iii) the sediment must be resuspended in the remaining fluid; (iv) the suspension must be transferred to and spread on a microscope slide; (v) a coverslip must be placed over the suspension on the slide; (vi) the slide must be focused under a microscope; and (vii) a number of fields of view must be searched and examined for the presence of abnormal numbers of red and white blood cells, epithelial cells, casts, bacteria, yeast, parasites, mucoid threads, crystals, etc., which compose urine sediment in various proportions depending upon the presence of disease. The steps of centrifugation (i), decantation (ii) and resuspension (iii) are used because the fluid sample is dilute. All these steps are currently performed manually. The manipulations involved frequently make the method messy and unpleasant. Spreading of the sediment suspension on the microscope slide often is uneven. When numerous sediments are viewed, prolonged peering into the eyepieces of a microscope becomes tiring. All these factors contribute to imprecision.

Other apparatus for handling biological specimens include the so-called Coulter counter. In this counter blood cells are passed in single file through an orifice and detected and counted by the manner in which they change the electric properties at the orifice. However, information from the Coulter counter is limited to the analysis of a single type of measurement. Where multiple parameter information is desired, the standard commercial way of obtaining it is by preparing a microscope slide with the cells fixed on an image plane and having a human operator or pattern recognition machine count statistically significant numbers of the cells as the cells are observed one-at-a-time on the slide through a microscope.

Other attempts have been made in recent years to provide optical analysis of particles flowing in a flow stream. For instance, Kay, et al., *Journal of Histochemistry and Cytochemistry*, Volume 27, page 329 (1979) shows a Coulter type orifice for moving cells in single file with the cells magnified on a vidicon. Additionally, Kachel, et al., *Journal of Histochemistry and Cytochemistry*, Volume 27, page 335, shows a device for moving cells in single file through a microscopic area where they are photographed. See also for instance *Flow Cytometry and Sorting*, Melaned et al., John Wiley & Sons 1979, Chapter 1.

U.S. patent application Ser. No. 146064 filed on May 2, 1980 now U.S. Pat. No. 4,338,024, issued on July 6, 1982 discloses an apparatus and a method for quantitative analysis of particle information.

However, none of the references cited heretofore teach or suggest a solution to the problem of analysis of particles in a dilute fluid sample, without the necessity of initially creating a concentrated sample through centrifugation, decantation and resuspension.

SUMMARY OF THE INVENTION

A method of analyzing particles from a fluid sample containing the particles, comprises distributing the sample over an extended area. A plurality of optical still images of the sample over the area are taken, with each optical image representing a different portion of the area. Each of the optical images is converted into an electronic image. The electronic images are composited to form one resultant electronic image.

BRIEF DESCRIPTION OF THE DRAWINGS

FIG. 1 is a perspective view of an apparatus which can be used with the method of this invention.

FIG. 2 is a plan view of the flow chamber in FIG. 1.

FIG. 3 is a cross-sectional view of the apparatus of FIG. 2 taken on the plane indicated at 3—3.

FIG. 4 is a schematic diagram of the electronic processor employed by the apparatus of FIG. 1.

DETAILED DESCRIPTION OF THE INVENTION

The method of the present invention comprises distributing a fluid sample, such as urine, over an extended area, such as smearing the sample over a microscope slide. A plurality of optical still images of the sample are taken, with each image representing a different portion of the slide. Thus, for example, the slide with the sample thereon may be mounted in a microscope and moved about such that a portion of the slide is in the imaging area. Each image will be of a different portion of the slide. Each of the optical images is converted to an electronic image. The plurality of electronic images are electronically composited to form one resultant electronic image. The one resultant electronic image may be further processed.

The method of the present invention may be practiced by using an apparatus 5, shown in FIG. 1. The apparatus 5 includes a body 10 containing a flow chamber having an inlet 12 for a fluid sample, such as urine, and an outlet 14 with a passageway 16 extending between them past an imaging area 18. The passageway 16 has an inlet with a conduit 20 adapted to be connected to a volume of saline solution 22. As illustrated in FIGS. 2 and 3, the inlet 12 for the urine sample has a needle 24 in the passageway 16 downstream from the conduit 20 with the needle 24 connected to a container 26 adapted to hold the urine sample to be analyzed. The urine sample flows in a direction from the inlet 12 to the outlet 14.

The cross-sectional area of the passageway 16 becomes progressively smaller as the passageway extends from the inlet 12 to the outlet 14 while at the same time the passageway 16 becomes much shallower and much wider. Thus, as illustrated in FIGS. 2 and 3 the passageway 16 has a width and depth of about 5,000 microns at the inlet 12 and a width and depth of about 500 microns at midpoint 28, and a depth of 100 microns with a width exceeding 5,000 microns at the examination area 18.

It will be appreciated that the fluid sample flowing through the examination area 18 is many times deeper than the largest cells which have a maximum dimension of about 20 microns, but with the flow passageway shaped in this way the fluid sample entering through the opening 12 is confined to a stable flow path of minimum shear in the examination area 18, and the particles in the fluid sample are oriented in that area with their maximum cross-sectional area visible in the plane of FIG. 2. The flow characteristic in the passageway 16 may be controlled by adjusting the fluid pressure in containers 22 and 26 either automatically or by adjusting the static heights thereof.

Preferably the fluid sample flowing in the examination area 18 has a cross-sectional area of minimum shear which it not substantially larger than the minimum cross-sectional area of the particles. Hence the particles are aligned in the fluid sample flowing in the examination area 18 with their minimum cross-sectional area extended transverse to the direction of flow. The term "minimum shear" is used herein to means "minimum velocity gradient" so that a particle moving in the stream tends to align itself with the direction of the stream much as a log floating down a river will align itself with the direction of flow where there is a flow gradient.

A microscope 30 is focused on the examination area 18 and the examination area 18 is illuminated from below by a strobe light 32 which is preferably a U.S. Scientific Instrument Corporation Model 3018 containing a 2UP1.5 lamp. The light 32 is directed at the microscope 30 in a direction substantially parallel to the thickness of the body 10. The stroke light 32 operates, preferably, at one-sixtieth of a second, thereby forming a series of still optical images at the microscope 30. The output of the microscope 30 is focused on a CCD camera 34 which is preferably a CCD camera model number TC1160BD manufactured by RCA. The CCD camera 34 converts each optical image into an electronic image. The CCD Camera 34 also segments each of the electronic images into a plurality of pixels, with each pixel corresponding to a defined portion of each image. The plurality of electronic images (each optical image is converted into an electronic image) are then composited to create one resultant electronic image. This may be done, for example, by summing all the pixels that correspond to the same defined portion of each image. The one resultant electronic image is an image of an apparent concentrated fluid sample, but without the necessity of physically creating a concentrated fluid sample. Moreover, the degree of apparent concentration is controlled by the number of images that are composited. Thus, an image of an apparent tend-fold concentration is accomplished by compositing ten images to form one resultant image. Since the degree of apparent concentration is controlled electronically, it should be obvious that with the method of the present invention, the image of the apparent concentration of the fluid sample may be varied with considerable ease.

The one resultant electronic image may be further processed, electronically, and displayed. Alternatively, each electronic image may be processed, electronically, prior to being composited to form the one resultant electronic image. One processor which may be employed, to process electronically either each electronic image or the one resultant electronic image, is the processor marketed as Image Analysis System Model C-1285 by Hamamatsu Systems, Inc., Waltham, Mass. Preferably, however, the output of the CCD camera 34 is connected to an electronic processor 36 which is illustrated in greater detail in FIG. 4 and includes a black and white television monitor 38 and a frame grabber 40 which stores still electronic images of the subject viewed by the CCD camera 34. The frame grabber 40 is preferably a Model FG08 frame grabber made by the Matrox Corporation of Montreal, the output of which is supplied to a video refresh memory 42 model RGB 256 made by Matrox Corporation which are both coupled to the multibus 44 of the central processing unit 46 which is preferably an Intel 80/20 computer. The multibus 44 is also coupled to a 48K random access memory 48 of Electronic Solutions, Inc., and a 16K dual port random access memory 50 model RM 117 of Data Cube Corporation. The output of the video refresh memory 42 is also coupled to a color monitor 52 which may be used to provide digitally enhanced video images of individual still frames for human examination.

The second output of the dual port ram 50 is connected to a multibus 54 which is connected to an Applied Micro Devices central processing unit 56, a 48K random access memory of Electronic Solutions, Inc. 58 and removable storage in the form of a floppy disc controller 60, such as an Advanced Micro Devices Model 8/8 and two units of Shugart floppy disc storage 62.

With the apparatus shown in FIG. 4, a number of specific methods, for the creation of the one resultant electronic image, is possible.

In the first alternative, fluid sample such as urine is entered into the inlet 12. The fluid is illuminated by the strobe light 32 and a plurality of optical still images of the sample are taken by the microscope 30. Because the fluid is translucent and the illumination is from below, the optical image will be of dark particles on a light background. The optical images are converted into electronic images which are then digitized and stored in memory 48. The one resultant electronic image, the composition of the plurality of electronic images, is formed by summing the digitized data of each electronic image with that data stored in memory 48.

In a variation of the above described method, prior to the data of the digitized image being stored in memory 48, the background data of each image is first removed, electronically. The pertinent information from each image may be collected and stored in one resultant electronic image.

In yet another alternative, urine is subjected into the inlet 12 as before. The urine is illuminated by the strobe light 32. However, using the well known technique of dark field illumination or phase contrast illumination, the optical image produced at the microscope 30 will be of light particles on a dark background. Each optical image is converted into an electronic image by the CCD camera 34. Due to the nature of the CCD camera 34, it retains the electronic image in the camera, if the electronic image is not read out. Thus, a subsequent electronic image (converted from an optical image) will be composited to the previous electronic image. The one resultant electronic image may therefore be formed at the CCD camera 34.

A wide variety of programming may be employed for further processing the one resultant electronic image with the apparatus of FIG. 4 depending upon the particular task which user wishes to perform.

For example with urine, in the method of the prior art, if chemical particles, such as phosphates are in the imaging area and obscure the view of the biological particles, the phosphate particles are removed chemically through the addition of hydrochloric acid. With the method of the present invention, however, the chemical particles may be removed electronically, i.e. through image processing techniques. If it is desired to remove particles of particular size, color or shape from view, this may be done electronically without repreparing the sample each time. Moreover, with the method of the present invention, biological particles, which heretofore may not be removed chemically, may be similarly electronically removed from the image. Thus a greater degree of flexibility is possible with the present invention.

It should be appreciated that there are many advantages to the method of the present invention. The first and foremost is that the analysis of particles of a dilute sample may be made without first physically creating a concentrated sample, with its attending problems of centrifugation, decantation and resuspension. The method of resuspension of the prior art results in overlap of the various particles or results in a biased image. With the method of the present invention, the fluid is more statistically representative of the particles with less likelihood of overlap of the particles, and there is no bias of the image. Next, it should be appreciated that the degree of apparent concentration may be varied electronically. In addition, the elimination of manual handling steps saves time, potential sources of error and offers biological safeguards (potentially infectious samples are analyzed with a minimum of human handling). Then too, consumable items, such as tubes, pipettes and microscope slides, are not used resulting in economic savings. Finally, with the image in electronic form, a number of imaging techniques may be used to further process the image, including the electronic removal of chemical and biological particles.

What is claimed is:

1. A method of displaying electronically concentrated microscopic particles, from a dilute biological fluid sample containing said particles, comprising:
   distributing said fluid sample over an extended area with substantially no particle overlapping other particles;
   forming a plurality of optical still images of said sample over said area, with each optical image representing a different portions of said area;
   converting each of said optical still images to an electronic image;
   compositing the images of the different particles from said electronic images to form one resultant electronic image;
   processing the resultant image; and
   displaying said processed image,
   whereby said processed image is an image of electronically concentrated microscopic particles.

2. A method of displaying electronically concentrated microscopic particles, from a dilute biological fluid sample containing said particles, comprising:
   distributing said fluid sample over an extended area substantially with no particle overlapping other particles;
   forming a plurality of optical still images of said sample over said area, with each optical image representing a different portion of said area;
   converting each of said optical still images to an electronic image;
   processing each of said electronic images;
   compositing the images of the different particles from said electronic images to form one resultant electronic image; and
   displaying said one resultant electronic image;
   whereby said resultant image is an image of electronically concentrated microscopic particles.

3. The method of claim 1 or 2 wherein said processing step is:
   electronically removing images of particles that are not desired for display.

4. The method of claim 1 or 2 further comprising the step of:
   segmenting each of said electronic images into a plurality of pixels, with each pixel corresponding to a defined portion of each image; and
   summing all the pixels that correspond to the same defined portion of each image.

5. The method of claim 1 wherein said compositing step is formed by a CCD camera.

6. The method of claim 1 wherein said fluid sample is urine and said particles are sediments.

7. The method of claim 2 further comprising the steps of:
   removing the background data from each electronic image; and
   collecting the pertinent information from each electronic image to form one resultant image.

8. A method of displaying electronically concentrated microscopic particles, from a moving dilute biological fluid sample containing said particles, comprising:
   moving said sample in a direction of flow;
   distributing said fluid sample over an extended area having a width and a thickness both measured perpendicular to the direction of flow, with the width many times the thickness, said sample distributed with substantially no particle overlapping other particles;
   illuminating said fluid at a predetermined location in the direction of flow, with said illumination directed in a direction substantially perpendicular to the direction of flow;
   forming a plurality of optical still images of said fluid sample, at said location with each optical image representing a different portion of said sample;
   converting each of said optical still images to an electronic image;
   compositing the images of the different particles from said plurality of electronic images to form one resultant electronic image;
   processing said one resultant image; and
   displaying said processed image,
   whereby said processed image is an image of electronically concentrated microscopic particles.

9. A method of displaying electronically concentrated microscopic particles, from a moving dilute biological fluid sample containing said particles, comprising:
   moving said sample in a direction of flow;
   distributing said fluid sample over an extended area having a width and a thickness both measured perpendicular to the direction of flow, with the width many times the thickness, said sample being distributed with substantially no particle overlapping other particles;
   illuminating said fluid at a predetermined location in the direction of flow, with said illumination directed in a direction substantially perpendicular to the direction of flow;
   forming a plurality of optical still images of said fluid sample, at said location, with each optical image representing a different portion of said sample;
   converting each of said optical still images to an electronic image;

processing each of said electronic images;

compositing the images of the different particles from said plurality of electronic images to form one resultant electronic image; and displaying said one resultant electronic image, whereby said resultant image is an image of electronically concentrated microscopic particles.

10. The method of claim 8 or 9 wherein said fluid sample is urine and the particles are sediments.

11. The method of claim 10 wherein said illuminating step is by stroboscopic illumination.

* * * * *